United States Patent [19]

Saito et al.

[11] Patent Number: 4,661,845
[45] Date of Patent: Apr. 28, 1987

[54] MICROORGANISM MONITORING APPARATUS

[75] Inventors: Toshio Saito; Kazuo Yukawa, both of Yokohama; Tomio Suzuki, Tokyo, all of Japan

[73] Assignee: Nishihara Environmental Sanitation Research Corporation Limited, Tokyo, Japan

[21] Appl. No.: 685,309

[22] Filed: Dec. 24, 1984

[30] Foreign Application Priority Data

| Dec. 23, 1983 [JP] | Japan | 58-197182 |
| Apr. 9, 1984 [JP] | Japan | 59-50752 |
| Jul. 10, 1984 [JP] | Japan | 59-141308 |
| Aug. 21, 1984 [JP] | Japan | 59-172393 |
| Sep. 3, 1984 [JP] | Japan | 59-132650 |

[51] Int. Cl.⁴ .......................................... H04N 7/18
[52] U.S. Cl. ..................................... 358/99; 358/93; 356/246; 250/576
[58] Field of Search ............... 358/99, 100, 93, 107, 358/901; 422/94, 95, 96.1; 435/291, 808; 350/536, 582, 584, 319; 356/244, 246; 250/576

[56] References Cited

U.S. PATENT DOCUMENTS

| 3,482,898 | 12/1969 | Van den Bosch | 350/536 |
| 3,609,236 | 9/1971 | Heilman | 350/584 X |
| 4,011,451 | 3/1977 | Nelson | 356/246 X |
| 4,165,179 | 8/1979 | Sato | 356/246 |
| 4,245,914 | 1/1981 | Clack | 350/582 X |
| 4,263,010 | 4/1981 | Randolph | 422/62 X |
| 4,346,404 | 8/1982 | Gatenbrink | 358/100 X |
| 4,502,407 | 5/1985 | Stevens | 358/99 X |

*Primary Examiner*—Howard W. Britton
*Assistant Examiner*—Victor R. Kostak
*Attorney, Agent, or Firm*—Michael N. Meller

[57] ABSTRACT

An apparatus for directly monitoring microorganisms present in a liquid comprises a window glass with one face in contact with the liquid. Near the other face is disposed a TV camera having an optical magnifying system for monitoring the microorganisms. A sample cell or a narrow space is formed on said one side of the window glass for direct introduction of a sample of the liquid. The sample is statically held in the cell even though the liquid is in movement. The sample is purged from the cell by feeding a cleaning fluid thereinto or by vibrating or otherside exerting physical movement on the cell, whereafter a new sample is introduced into the cell. Purging of the sample cleans the cell and is prevents it from being smudged with dregs, dirt or the like included in the liquid.

34 Claims, 20 Drawing Figures

FIG. 6
FIG. 8
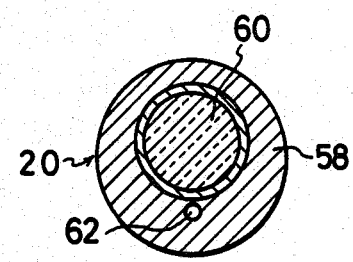
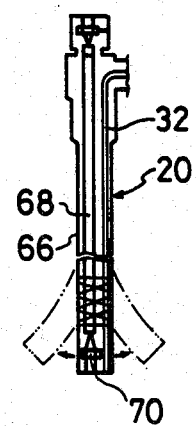
FIG. 7
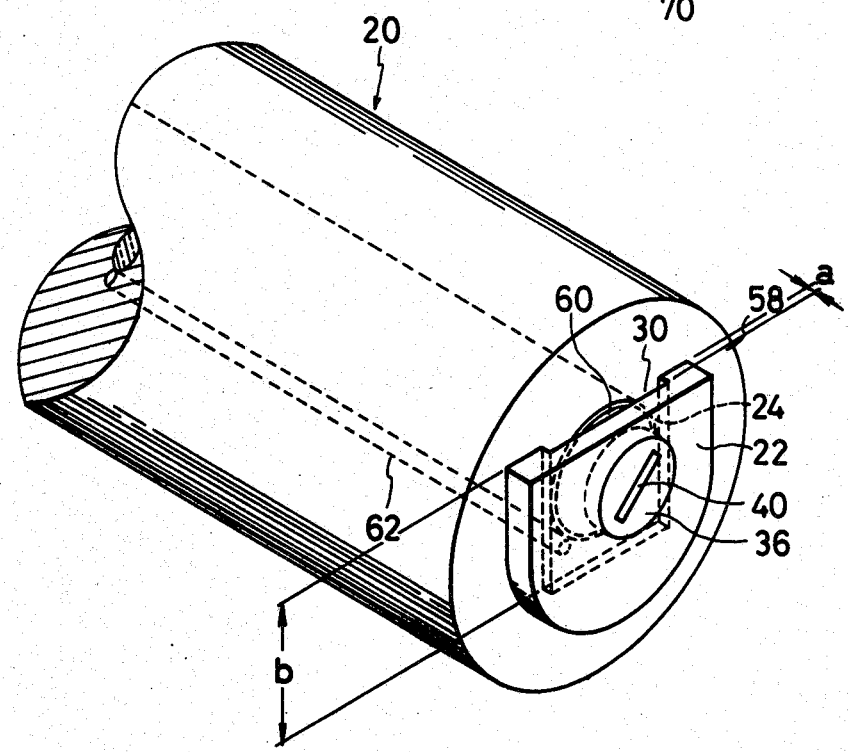

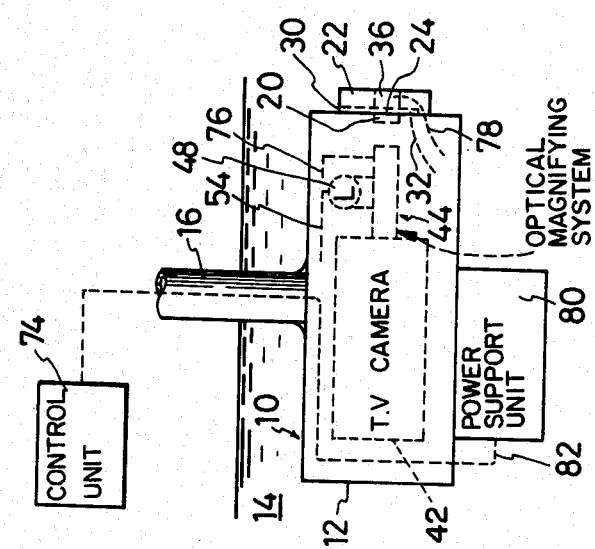
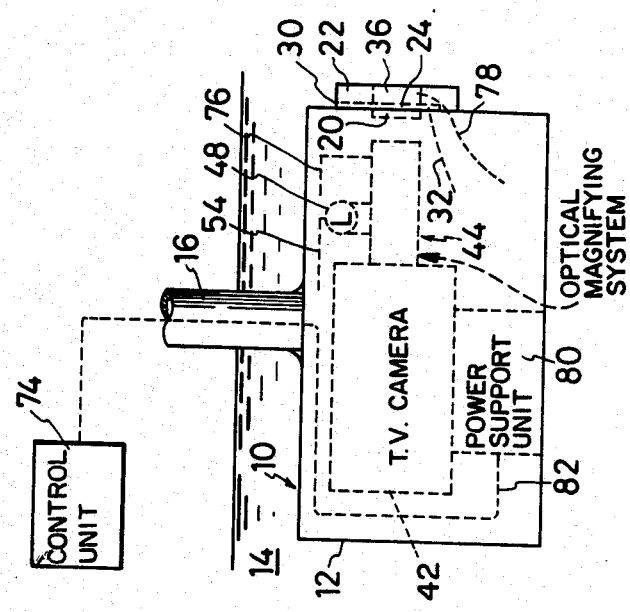

MICROORGANISM MONITORING APPARATUS

BACKGROUND OF THE INVENTION

1. Field of the Invention

The present invention relates to a microorganism monitoring apparatus, and more particularly to an apparatus for directly monitoring microorganisms present in a liquid.

2. Description of the Prior Art

In a microbiological process such as one wherein a waste water such as sewage is treated by bacteria or wherein an antibiotic substance is produced by fermentation, it is necessary to monitor the state of the microorganism (in the former, the state of bacteria flocs and the species of *protozoa, metazoa;* in the latter, the state of molds) in order to learn the treatment condition of the waste water or the stage of fermentation. Conventionally, this observation is performed by microscopic examination of a sample taken from the waste water or the fermented liquid. Obviously, however, it is troublesome to take such samples and to prepare specimens for microscopic observation. Also, in the case of microscopic observation, there is the possibility that the state of the microorganism actually observed may not be the same as those in the liquid in the vessel because, for example, aggregations of the microorganisms may be broken up when the specimen is prepared.

In view of the drawbacks of the conventional method mentioned above, a microorganism monitoring apparatus by which the microorganism present in the liquid contained in the vessel can be directly observed and monitored has previously been proposed and is disclosed, for example, in JAPANESE PATENT PUBLIC DISCLOSURES No. 52(1977)-89942 and No. 52(1977)-99839 which were filed on Jan. 23, 1976 and Feb. 17, 1976, respectively.

JAPANESE PATENT PUBLIC DISCLOSURE No. 52(1977)-89942 discloses a microorganism monitoring apparatus comprising a cylindrical housing extending through a wall of the vessel and having a window glass mounted on its inner end so that one face of the window glass is adapted to be contacted with the liquid in the vessel, an optical magnifying system disposed within the cylindrical housing and having an objective lens which is opposed to the other face of the window glass, a TV camera provided opposite to an eye piece of the optical magnifying system, a monitor TV associated with the TV camera, and a strobo light source having a light guide which extends through the wall of the vessel into the liquid so that an end face of the light guide is directed to the one face of the window glass. In this apparatus, although the microorganisms are in motion in the liquid contained in the vessel, a static image of the microorganisms which pass through the space between the end face of the light guide and the one face of the window glass can be displayed on the monitor TV due to use of the strobo flash emitted from the strobo light source. In this way, it is possible to directly observe and monitor the microorganisms in motion in the liquid contained in the vessel. However, in this apparatus, it is impossible to continuously observe and monitor the microorganisms over time because the microorganism cannot be captured in the space between the end face of the light guide and the one face of the window glass. Also, when the end face of the light guide and/or the one face of the window glass are smudged with, for example, dregs, dirt or the like included in the liquid, it is impossible to obtain a clear image on the monitor TV.

JAPANESE PATENT PUBLIC DISCLOSURE No. 52(1977)-99839 discloses a microorganism monitoring apparatus comprising a first closed housing which is adapted to be submerged in the liquid contained in the vessel, an optical magnifying system provided within the first closed housing so that an objective lens thereof is adapted to be directly contacted with the liquid, a TV camera provided within the first closed housing and associated with the optical magnifying system, a second closed housing having a window glass opposed to the objective lens of the optical magnifying system and movably supported by the first closed housing so that the space between the window glass and the objective lens can be adjusted, and a strobo light source disposed within the second closed housing so that it is opposed to the window glass. Said DISCLOSURE No. 52(1977)-99839 also discloses a microorganism monitoring apparatus comprising a cylindrical housing integrally formed in a wall of the vessel containing the liquid, an optical magnifying system provided within the cylindrical housing so that an objective lens thereof is adapted to be directly contacted with the liquid, a TV camera associated with the optical magnifying system, a strobo light source having a light guide which extends through the wall of the vessel into the liquid so that an end face of the light guide is directed to the objective lens, and the strobo light source movable together with the light guide so that the space between the end face of the light guide and the objective lens of the optical magnifying system can be adjusted. In these apparatuses, the space between the window glass and the objective lens or the end face of the light guide and the objective lens is narrowed down so that the microorganisms passing therethrough are temporarily captured in the space during the passage, whereby it is possible to observe and monitor the microorganism in a static condition in spite of the fact that the microorganisms are in motion in the liquid contained in the vessel. However, in these apparatuses, it is also impossible to prevent the window glass of the second closed housing, the end face of the light guide and/or the objective lenses from being smudged with dregs, dirt or the like included in the liquid. Of course, when they are smudged with the dregs, dirt or the like, it is impossible to obtain a clear image on the monitor TV.

SUMMARY OF THE INVENTION

Accordingly, it is a principal object of the present invention to provide an apparatus for directly monitoring microorganisms present in a liquid, whereby the microorganisms can be continuously observed and monitored in a static condition over the passage of time in spite of the fact that the microorganisms are in motion in the liquid, and it is ensured that a clear image of the microorganisms is always obtained on a display device.

It is a further object of the present invention to provide a microorganism monitoring apparatus as mentioned above wherein there is provided a sample cell or a narrow space which is disposed within the liquid to statically hold a sample introduced from the liquid into the sample cell or the narrow space.

It is a still further object of the present invention to provide the microorganism monitoring apparatus as mentioned above wherein a plate member forming the sample cell or the narrow space is provided with a reflector means so as to simplify the light source system for observing and monitoring the sample held in the sample cell.

It is a still further object of the present invention to provide the microorganism monitoring apparatus as mentioned above wherein a sample can be taken at any point within the liquid contained in the vessel.

It is a still further object of the present invention to provide the microorganism monitoring apparatus as mentioned above in a manner suitable for use in a liquid that must be protected from the invasion of sundry germs or a liquid to be treated by anaerobic bacteria.

It is a still further object of the present invention to provide the microorganism monitoring apparatus as mentioned above wherein an image of the microorganisms can be adjustably magnified.

In order to achieve the principal object mentioned above, the microorganism monitoring apparatus according to the present invention comprises:

transparent window means one face of which is adapted to be contacted with the liquid;

a plate member disposed opposite to the one face of said transparent window means so as to form a narrow sample cell between said one face and said plate member, a part of said sample cell being open to permit introduction of a sample from the liquid thereinto;

a tube member one end of which is connected to said sample cell and the other end of which can be connected to a pump to feed a cleaning fluid to said sample cell for purging the sample held therein;

a light source for directing a light beam out the sample held in said sample cell;

an optical magnifying system disposed opposite to the other face of said transparent window means to magnifying an image of the sample illuminated by said light beam; and means for observing the image magnified by said optical magnifying system.

In this arrangement, the light source may be provided on the side of the other face of the transparent window means, i.e. on the side of the window means opposite that in contact with the liquid. When this arrangement is used, the plate member is provided with a reflector means on the face thereof opposed to said one face of the transparent window means. The optical magnifying system is utilized to guide the light beam from the light source toward the reflector means, and receives the light beam reflected by the reflector means. It is advantageous to utilize the optical magnifying system for guiding the light beam toward the reflector means because this makes it possible to simplify the light source system. That is, if the reflector means is not used and if the optical magnifying system is not utilized for guiding the light beam, it is necessary to use an additional light guide for directing the light beam to the one face of the transparent window means, as in the case of the above-mentioned DISCLOSURES No. 52(1977)-89942 and No. 52(1977)-99839. On the other hand, the light source may be provided on the face of the plate member which is opposed to the one face of the transparent window means. In this case, of course, the optical magnifying system directly receives the light beam from the light source through the transparent window means.

When it is desired to enable samples to be taken at any point within the liquid, the transparent window means is mounted on a wall of a closed housing which is adapted to be submerged in the liquid. In this case, the optical magnifying system, the tube member and a TV camera which forms a part of the observing means are housed within the closed housing. When the light source is provided on the side of the other face of the transparent window means, it is also housed within the closed housing.

The magnifying power of the optical magnifying system may be adjustable. In this case, it is preferable to movably mount a reflector means on the plate member so that the space between the reflector means and the one face of the transparent window means can be adjusted in response to the adjustment of the magnifying power of the optical magnifying system. In this way, an image of the microorganisms can be clearly and stably displayed on the display device, a monitor TV. Also, when the magnifying power of the optical magnifying means is adjustable, it is advantageous for the TV camera to be movable together with the optical magnifying system with respect to the transparent window means so that the field of view of the TV camera can be changed and so that the focus of the optical magnifying system can be shifted.

When the liquid is contained in a vessel, the transparent window means can be mounted on the wall of the vessel containing the liquid. In this case, the transparent window means may comprise a cylindricl optical glass which extends through the wall of the vessel and which guides an image from its one end face to its other end face.

Furthermore, the transparent window means may comprise a flexible bundle of optical fibers having its free end face immersed in the liquid through the surface thereof, thus permitting selection of the sampling point in the liquid.

It is possible to use water, air or the like as the cleaning fluid for purging the sample held in the sample cell. When the microorganism monitoring apparatus is utilized in a sewage treatment plant, it is also possible to use a part of the sewage as the cleaning fluid for purging the sample held in the sample cell. On the other hand, if the microorganism monitoring apparatus is utilized in a bioreactor, it is expedient to use a raw material being fed into the bioreactor, a product obtained from the bioreactor and/or the liquid contained in the bioreactor as the cleaning fluid for purging the sample. If water or air is used as the cleaning fluid for purging the sample, this fluid has to be sterilized because, in general, a bioreactor has to be protected against the invasion of sundry germs.

When the sample is purged from the sample cell by the cleaning cell, the inner surfaces of the sample cell are, of course, cleaned and prevented from being smudged with dregs, dirt or the like included in the sample.

In another aspect of the present invention, the microorganism monitoring apparatus comprises:

transparent window means one face of which is adapted to be contacted with the liquid;

a plate member with a magnet disposed opposite to the one face of said transparent window means and being movable perpendicularly to said one face;

spacer means provided between said plate member and the one face of said transparent window means so as to form a narrow intervening space for introducing a sample from the liquid thereinto;

an electromagnetic coil provided on the side of the other face of said transparent window means to move said plate member perpendicularly to the one face of said transparent window means for purging the sample held in said narrow space and for introducing a new sample thereinto;

a light source for directing a light beam onto the sample held in said narrow space;

an optical magnifying system disposed opposite to the other face of said transparent window means to magnify an image of the sample illuminated by said light beam; and means for observing the image magnified by said optical magnifying system.

In this arrangement, the spacer means may comprise at least three projections formed on either the circumference of the transparent window means or the plate member.

In the same way as in the first mentioned-apparatus, the light source may be provided on either the side of the other face of the transparent window means or the face of the plate member which is opposed to the one face of the transparent window means. Of course, when the light source is provided on the side of the other face of the transparent window means, the plate member has a reflector means provided on its face opposed to the one face of the transparent window means.

Similarly, if it is desired to be able to obtain sample at any point from the liquid contained in the vessel, the transparent window means is mounted on a wall of a closed housing which is adapted to be submerged in the liquid. In this case, the optical magnifying system and a TV camera which forms a part of the observing means are housed within the closed housing. When the light source is provided on the side of the other face of the transparent window means, it is also housed within the closed housing. On the other hand, when the liquid is contained in a vessel the transparent window means may be mounted on the wall of the vessel containing the liquid. Also, the transparent window means may comprise a flexible bundle of optical fibers having its free end face immersed in the liquid through the surface thereof.

When the plate member with magnet is vibrated by the electromagnetic coil, not only is the sample held in the narrow space purged therefrom, but also the one face of the transparent window means and the face of the plate member opposed thereto are cleaned and prevented from being smudged with dregs, dirt or the like included in the sample. Since the sample held in the narrow space is purged therefrom without using a cleaning fluid such as air or water, this microorganism monitoring apparatus is suitable for use in a liquid that requires protection from invasion of sundry germs or a liquid to be treated with anaerobic bacteria.

Furthermore, in still an other aspect of the present invention, the microorganism monitoring apparatus comprises:

an elongate housing including a light guide and an optical image guide therewithin and having a free end face adapted to be contacted with the liquid, said light guide and said optical image guide extending to the free end face of said elongate housing so that the free end faces of said light guide and said optical image guide are exposed at the free end face of said elongate housing;

a plate member formed as an extended portion of the free end of said elongate housing and disposed opposite to the free end face of said elongate housing so as to form a sample cell therebetween, a part of said sample cell being open to permit introduction of a sample from the liquid thereinto;

a refractor means supported by said plate member and having a flat face which is opposed to the free end face of said optical image guide so as to form a narrow space therebetween;

a light source provided on the other end face of said light guide;

said refractor being arranged in such a manner that after a light beam emitted from said light source passes through said light guide, it is introduced into said optical image guide through the exposed end face thereof;

an optical magnifying system provided on the other end face of said optical image guide to magnify an image of the sample illuminated by the light beam introduced into said optical image guide;

means for observing the image magnified by said optical magnifying system; and means for purging the sample held in said sample cell and for introducing a new sample thereinto.

When this microorganism monitoring apparatus is utilized in a liquid requiring protection from invasion of sundry germs or a liquid be treated with anaerobic bacteria, the purging introducing means is constituted by an ultrasonic vibrator provided in the sample cell or a device for rotating the refractor means. In this case, the sample held in the sample cell can be purged therefrom without using a cleaning fluid such as air or water and a new sample can be introduced thereinto, while the inner surfaces of the sample cell and the flat face of the refractor means are cleaned and prevented from being smudged with dregs, dirt or the like included in the sample.

In the same way as in the first-mentioned apparatus, the purging introducing means may comprise a tube member one end of which is connected to the sample cell and the other end of which can be connected to a pump to feed a cleaning fluid to the sample cell for purging the sample held therein. The tube member may be housed within the elongate housing.

It is expedient to form the elongate housing, the light guide and the optical image guide from flexible materials to permit selection of the sampling point in the liquid. When the tube member is housed within the elongate housing, it is also of course formed from a flexible material.

The above and further objects and novel features of the present invention will be more fully apparent from the following detailed description when the same is read in connection with the accompanying drawings. It is to be understood, however, that the drawings are not intended as a definition of the limits of the present invention.

BRIEF DESCRIPTION OF THE DRAWINGS

FIG. 6 is a cross-sectional view of the transparent window means shown in FIG. 5;

FIG. 7 is a partial perspective view of the transparent window means shown in FIG. 5;

FIG. 8 is a longitudinal sectional view of an optical fiberscope forming the transparent window means, in accordance with still another embodiment of the present invention;

FIG. 12 is an elevational view showing a modified embodiment of FIG. 11;

FIG. 13 is an elevational view showing another modified embodiment of FIG. 11;

Referring to FIGS. 1 and 2, a microorganism monitoring apparatus constructed according to the present invention is designated by the reference numeral 10 and comprises a closed cylindrical housing 12 which is adapted to be submerged in a liquid 14 contained in a vessel (not shown) in which the liquid is treated by microorganisms. In this embodiment, the vessel is an aeration tank in which a liquid such as sewage is treated by bacteria.

The closed cylindrical housing 12 has a hollow support rod 16 which extends vertically from an intermediate portion between the end faces of the cylindrical housing 12. The upper end portion (not shown) of the support rod 16 is connected to and is suspended from a device (not shown) for displacing the housing 12 up and down. The device may be a crane by which the housing 12 can be freely moved within the sewage 14. The closed cylindrical housing 12 also has two plate-like stabilizers 18 which are secured to the housing 12 and the rod 16 at the corner regions formed therebetween. When the housing 12 is submerged in the sewage 14 while the sewage is being aerated, it is stabilized by the stabilizers 18. The stabilizers 18 prevent the rod 16 from becoming entangled with filamentary dusts such as hairs included in the sewage 14.

Figure 3:
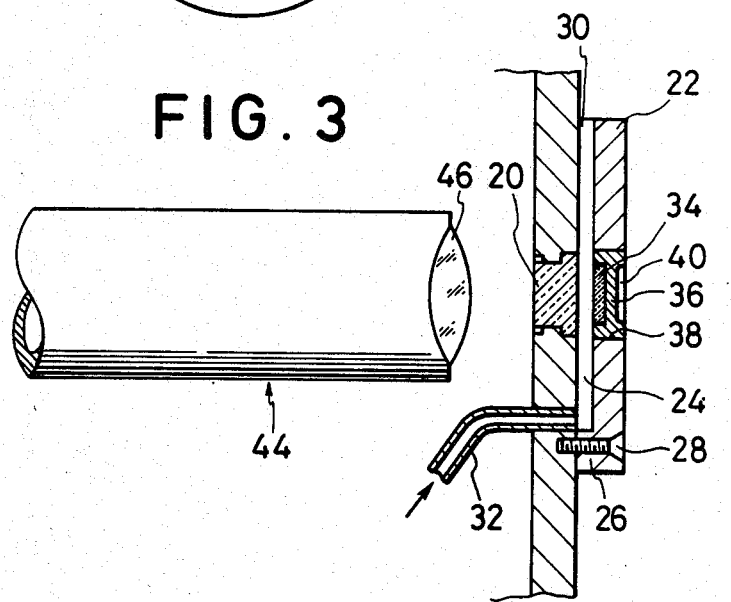
FIG. 3 is a partial longitudinal sectional view of the cylindrical closed housing shown in FIG. 1.

The closed cylindrical housing 12 is provided with transparent window means 20 at its one end face, as shown in FIG. 3. In this embodiment, the transparent window means 20 is formed from a window glass one face of which is adapted to be in contact with the sewage 14 and the other face is exposed to the interior space of the closed housing 12. As best shown in FIG. 3, a plate member 22 is disposed opposite to the one face of the window glass 20, namely, the outer face thereof, so as to form a narrow sample cell 24 between the outer face of the window glass 20 and the plate member 22. In order to form the sample cell 24, a U-shaped ridge 26 is integrally formed on the face of the plate member 22 which is opposed to the outer face of the window glass 20. As shown in FIG. 3, the plate member 22 is securely mounted on the end face of the cylindrical housing 12 by means of screws 28 (only one shown) which are threaded into the end face of the housing 12 through the U-shaped ridge 26 of the plate member 22, whereby the sample cell 24 is defined by the end face of the housing 12 inclusive of the outer face of the window glass 20, the face of the plate member 22 which is opposed to said end face, and the inner surface of the U-shaped ridge 26 so that the sample cell 24 has an upper opening 30 through which a sample is introduced from the sewage 14 and is also purged from the sample cell 24.

In order to purge the sample from the sample cell 24, a tube member 32 is provided within the closed housing 12. One end of the tube member 32 is connected to the sample cell 24. When air is used as the cleaning fluid, the other end (not shown) of the tube member 32 can be connected to a pump or an air compressor (not shown) to feed a cleaning air to the sample cell 24. After the feeding of the air is stopped, a new sample is introduced into the sample cell 24 through the opening 30. When water or a part of the sewage 14 is used as the cleaning fluid, the other end of the tube member 32 can be selectively connected to a vacuum source (not shown) such as an aspirator for introducing a new sample from the sewage 14 into the sample cell 24 through the upper opening 30 thereof. Especially when the part of the sewage 14 is used as the cleaning fluid, it may be introduced into the sample cell 24 through the opening 30 thereof so that it is returned to the body of the sewage 14 through the tube member 32.

As shown in FIG. 3, the plate member 22 has reflector means 34 provided at its face which is opposed to the outer face of the window glass 20. In this embodiment, the reflector means 34 comprises a mirror which is detachably mounted on the plate member 22. That is, the mirror 34 is supported by a disc-like insert 36 which has a thread formed on its peripheral surface, whereby the insert 36 supporting the mirror 34 is threaded into a threaded bore 38 formed at the center of the plate member 22. The disc-like insert 36 has a slot 40 for receiving a tool such as a screwdriver (not shown). According to this arrangement, the insert 36 supporting the mirror 34 can be easily detached from the plate member 22 for cleaning the surface of the mirror 34. Also, the disc-like insert 36 supporting the mirror 34 may be driven by a servomotor (not shown) associated therewith so that a space between the window glass 20 and the mirror 34 can be adjusted for the reasons which will be stated in connection with FIG. 11. Furthermore, the plate member 22 per se may be moved in place of the movement of the insert 36.

Figure 1:
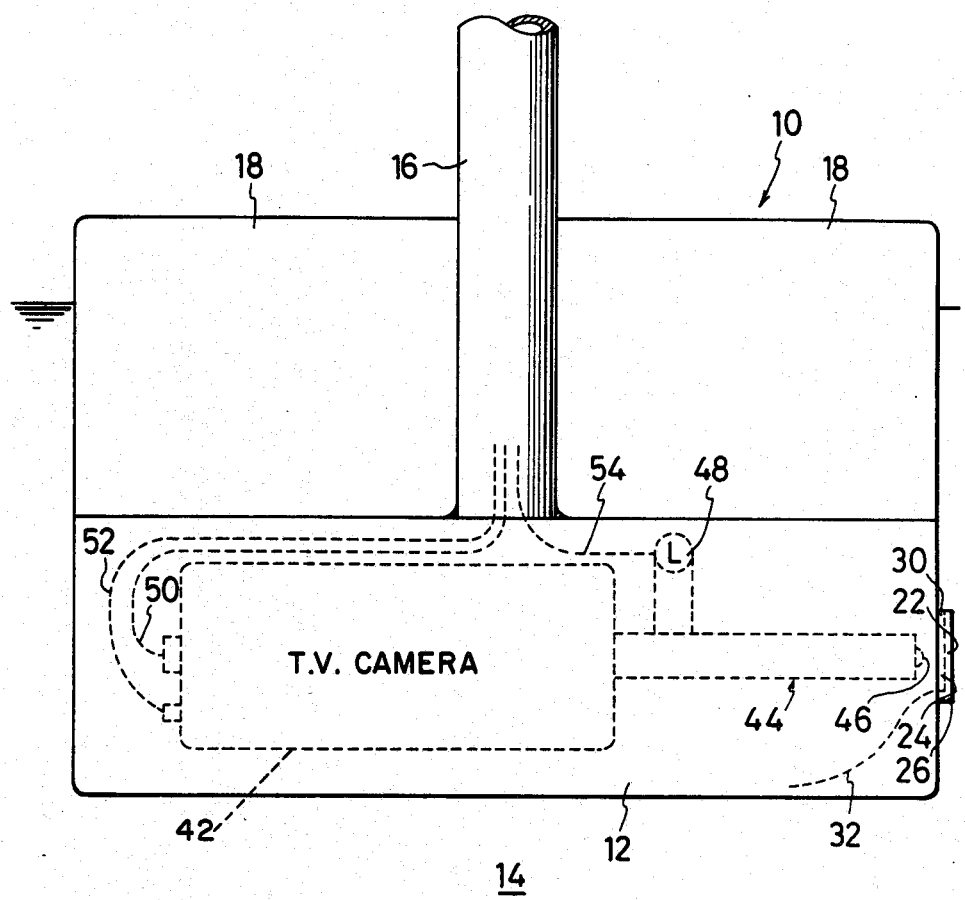
FIG. 1 is an elevational view showing a cylindrical closed housing which is adapted to be submerged in a liquid contained in a vessel and in which the present invention is embodied.
Figure 2:
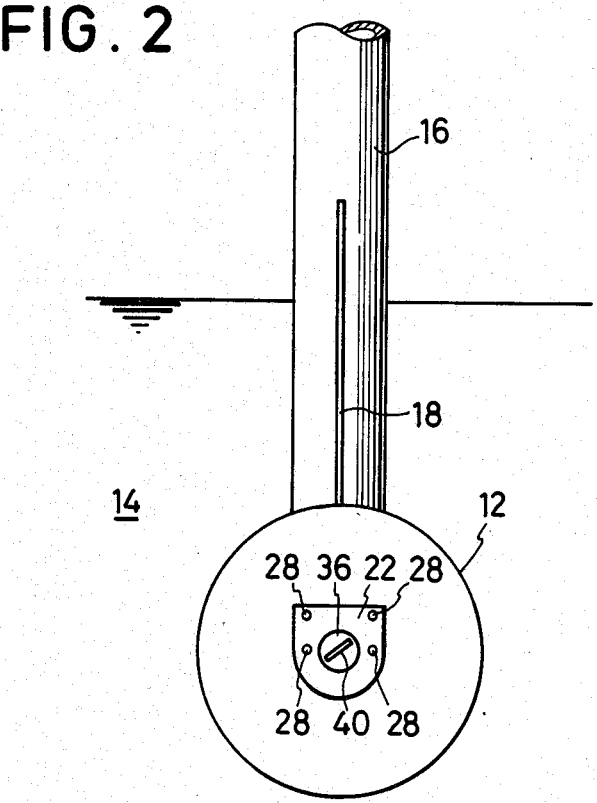
FIG. 2 is an end view of the cylindrical closed housing shown in FIG. 1.

As shown in outline in FIG. 1, a TV camera 42 is housed within the closed housing 12 and is suitably supported therewithin. The TV camera 42 has an optical magnifying system 44 combined therewith, an objective lens 46 of which is opposed to the inner face of the window glass 20, the optical magnifying system 44 is focused at a point in the vicinity of the outer face of the window glass 20, that is, at a point between a point 1μ away from the outer face of the window glass and a point 1000μ away from said outer face. A light source 48 is also housed within the closed housing 12 and is combined with the optical magnifying system 44. A light beam emitted from the light source 48 is guided toward the mirror 34 through a half mirror provided within the optical magnifying system 44 and is reflected by the mirror 34 to be received by the optical magnifying system 44.

A display device (not shown in this embodiment) such as a monitor TV is installed at a monitoring station and is connected to the TV camera 42 by means of a cable 50 which extends from the TV camera 42 to the monitor TV through the inner passage of the hollow support rod 16. The TV camera 42 is also connected to an outside electric power source (not shown) by means of a wire 52 which also extends through the inner passage of the hollow support rod 16. Furthermore, the light source 48 is also connected to the outside electric power source by means of a wire 54 which similarly extends through the inner passage of the hollow support rod 16. In addition, the tube member 32 also extends through the inner passage of the hollow support rod 16 and the other end thereof is connected to the pump for purging the sample, which is located outside of the closed housing.

Figure 4:
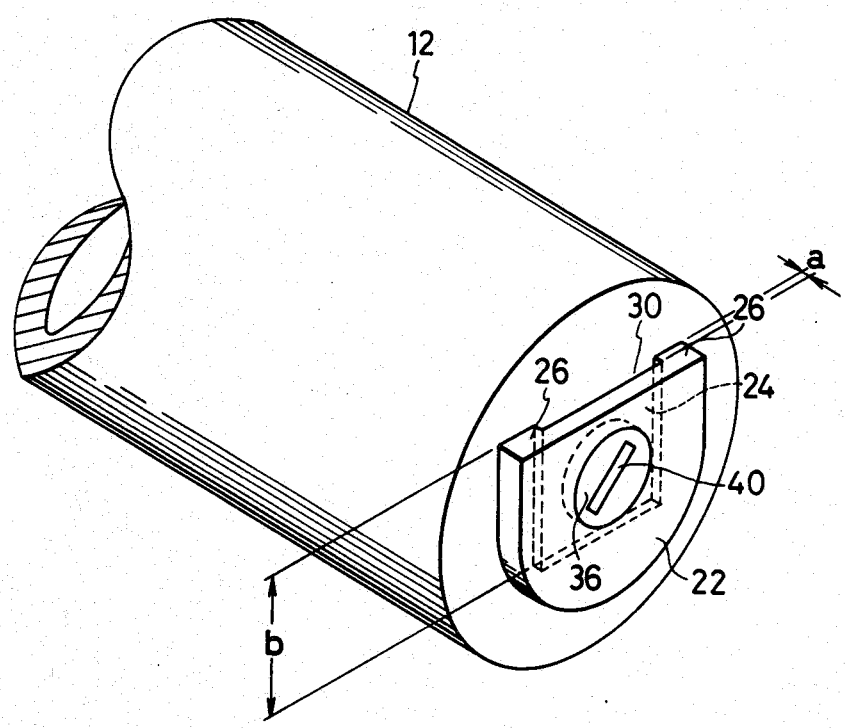
FIG. 4 is a partial prespective view of the cylindrical closed housing shown in FIG. 1.

Referring to FIG. 4, the thickness and height of the sample cell 24 are designated by the reference symbols a and b, respectively. The thickness a is preferably less than 3 mm and the height b is preferably greater than 5 mm so that the sample held in the sample cell 24 is not affected by the turbulence of the aerated sewage 14, whereby the sample can be statically held in the sample cell 24.

In operation, the light beam emitted from the light source 48 is guided toward the mirror 34 through the half-mirror provided within the optical magnifying system 44. The light beam is reflected by the mirror 34 and is then received by the optical magnifying system 44 after it passes through the window glass 20. The resulting image carried by the light beam, that is, the image of the bacteria statically held in the vicinity of the outer face of the window glass, is magnified by the optical magnifying system 44. The magnified image is then picked up by the TV camera 42 and displayed on the monitor TV, whereby the bacteria can be continuously observed and monitored in the static condition over the passage of time. If it is desired to monitor the bacteria at another point within the sewage 14, the closed housing is moved to that point by the device for displacing it up and down. Thereafter, the sample held in the sample cell 24 is purged therefrom by feeding a cleaning fluid such as air, water or a part of the sewage 14 into the sample cell 24 and a new sample is then introduced from the sewage 14 into the sample cell 24 in the manner as stated hereinbefore. The bacteria present in the new sample are observed and monitored by the monitor TV in the same manner as mentioned above. When the sample held in the sample cell 24 is purged therefrom, the interior surfaces of the sample cell 24, in particular, the outer face of the window glass 20 and the surface of the mirror 34, are cleaned and prevented from being smudged with dregs, dirt or the like included in the sample so that a clear image can be always obtained on the monitor TV. It is apparent that the purging may also be performed only for the purpose of cleaning the sample cell 24 rather than for elimination of the sample therefrom.

Figure 5:
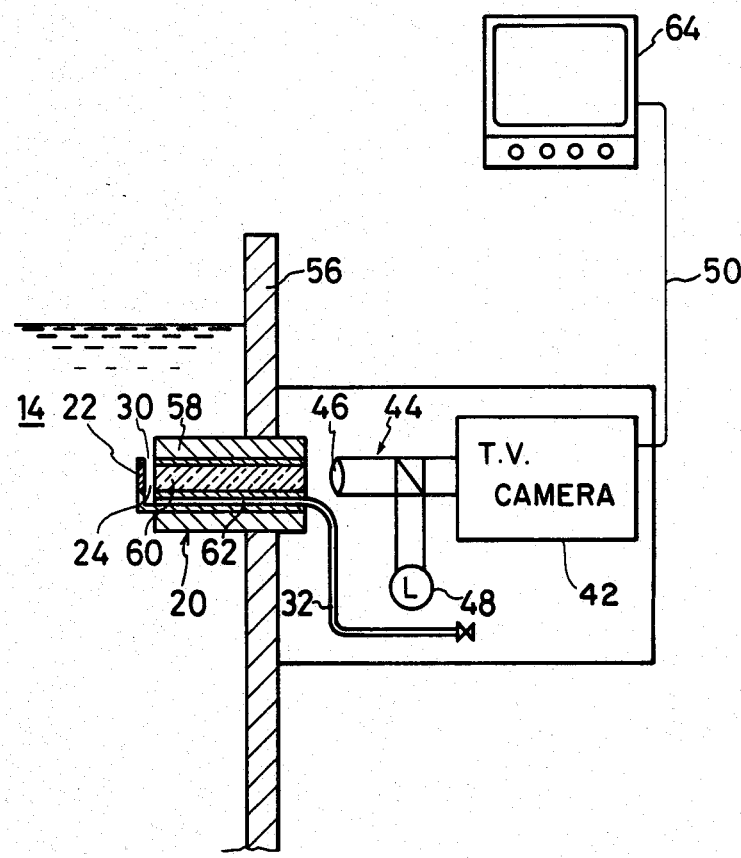
FIG. 5 is a diagrammatic view showing another embodiment of the present invention, wherein a transparent window means is mounted in a wall of a vessel in which liquid is received.

FIGS. 5 to 7 show another embodiment of the microorganism monitoring apparatus according to the present invention, wherein like reference numerals are used to designate the same elements as in the embodiment shown in FIGS. 1 to 4.

In this embodiment, transparent window means 20 is sealingly mounted and supported in the wall 56 of the vessel containing the sewage 14. The transparent window means 20 comprises a cylindrical member 58 extending through the wall 56 of the vessel and a cylindrical optical glass 60 eccentrically extending through the cylindrical member 58. The diameter of the cylindrical optical glass 60 is preferably within the range between 0.5 mm and 5 mm. As shown in FIG. 5, one end face of the cylindrical optical glass 60 is adapted to be in contact with the sewage 14 and is flush with the corresponding end face of the cylindrical member 58, and the other end face of the optical glass 60 is flush with the other end face of the cylindrical member 58. The cylindrical optical glass 60 may be formed of an optical image guide element which serves to guide an image from its one end face to its other end face without magnification. Such an optical image guide element per se is well known in this field. More specifically, the optical image guide element has a gradient n(r) of refractive index as shown by the following formula:

$$n(r) = n_0(1 - \tfrac{1}{2}Ar^2)$$

wherein n is the refractive index at the optical axis of the optical image guide element; A is the gradient constant of the refractive index; and r is the distance from the optical axis of the optical image guide element.

A plate member 22 is disposed opposite to the one end face of the cylindrical optical glass 60 so as to form a narrow sample cell 24, with the sample cell 24 having an upper opening 30 through which a sample is introduced from the sewage 14 and is also purged from the sample cell 24. The plate member 22 can be formed in the same manner as in the embodiment shown in FIGS. 1 to 4 and is securely mounted on the corresponding end face of the cylindrical member 58 by means of screws or the like. Similarly, as shown in FIG. 7, the plate member 22 has a disc-like insert 36 which supports a mirror (not shown) opposed to the corresponding end face of the cylindrical optical glass 60 and which has a slot 40 for receiving a tool such as a screwdriver (not shown).

The cylindrical member has a passage 62 formed therewithin, one end of which is connected to the sample cell 24 and the other end of which is connected to one end of a tube member 32. The other end of tube member 32 can be connected to a pump or an air compressor (not shown) to feed a cleaning air into the sample cell 24 for purging the sample held therein through the upper opening 30. Similarly, when water or a part of the sewage 14 is used as the cleaning fluid, the other end of the tube member 32 can be also connected to a vacuum source (not shown) such as an aspirator for introducing a new sample from the sewage 14 into the sample cell 24 through the upper opening 30.

Referring to FIG. 7, the thickness and height of the sample cell 24 are designated by the reference symbols a and b, respectively. The thickness a is preferably less than 3 mm and the height b is preferably greater than 5 mm, whereby the sample can be statically held in the sample cell 24.

As shown in FIG. 5, an optical magnifying system 44 provided outside the vessel containing the sewage 14 has an objective lens 46 which is opposed to the corresponding end face of the cylindrical optical glass 60. The optical magnifying system 44 is focused at a point in the vicinity of the corresponding end face of the cylindrical optical glass 60. The optical magnifying system 44 is combined with a TV camera 42 which is connected to a display device 64 such as a monitor TV. The optical magnifying system 44 has a light source 48 combined therewith and a half mirror for directing the emitted light beam to the mirror which is supported by the insert 36.

It is apparent that the microorganism monitoring apparatus shown in FIGS. 5 to 7 can be operated in the same manner as in the embodiment shown in FIGS. 1 to 4 except that the sampling point is fixed due to the transparent window means 20 being mounted on the vessel wall 56. It is also apparent that air, water or a part of the sewage 14 can be used as the cleaning fluid.

Figure 9:
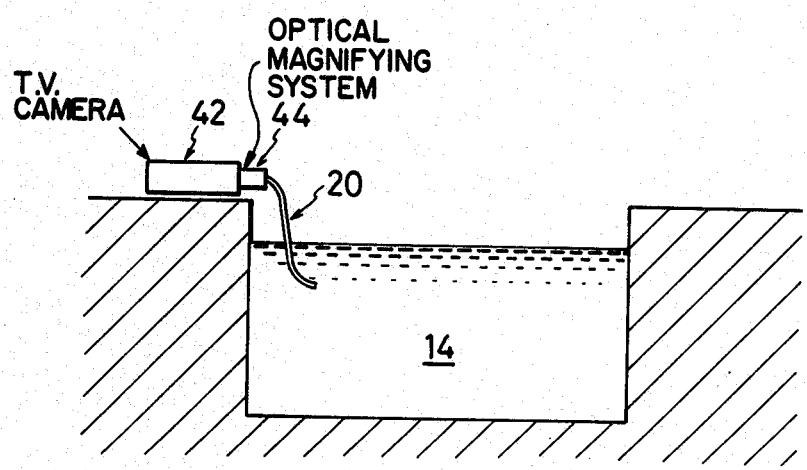
FIG. 9 is a diagrammatic view in which the optical fiberscope of FIG. 8 is used in accordance with the present invention.
Figure 10:
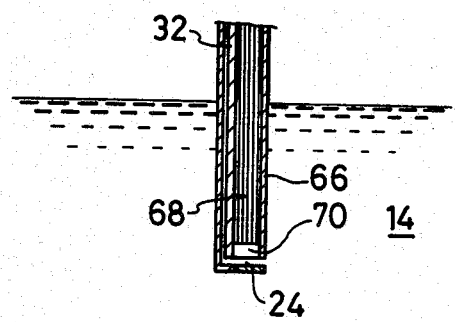
FIG. 10 is a partial longitudinal sectional view of the optical fiberscope shown in FIG. 8, wherein the free end thereof is submerged in sewage.

FIGS. 8 to 10 show still another embodiment of the microorganism monitoring apparatus according to the present invention, wherein like reference numerals are also used to designate the same elements as in the embodiments mentioned above.

In this embodiment, transparent window means 20 is formed as an optical fiberscope, as shown in FIG. 8. The optical fiberscope 20 comprises an elongate flexible housing 66, a flexible bundle 68 of optical fibers housed therein, and an objective lens 70 disposed on the free end face of the flexible bundle 68 of optical fibers and supported by the free end of the elongate flexible housing 66. As shown in FIG. 9, the other end of the elongate flexible housing 66 is connected to a optical magnifying system 44 so that the other end face of the flexible bundle 68 of optical fibers is opposed to an objective lens of the optical magnifying system 44. The optical magnifying system 44 is combined with a TV camera 42 which is located near the top opening of the vessel containing the sewage 14, which is shown to be sunk into the ground. The TV camera is, of course, connected to a display device such as a monitor TV.

As best shown in FIG. 10, a plate member 22 is integrally formed at the free end of the elongate flexible housing 66 and is disposed opposite to the corresponding end face of the objective lens 70 so as to form a sample cell 24. A part of the sample cell 24 is open, as designated by the reference numeral 30, for introducing a sample from the sewage 14 thereinto and for purging the same therefrom.

In order to introduce the sample into the sample cell 24 and purge the same therefrom, a flexible tube member 32 is also housed within the elongate flexible housing 66. One end of the flexible tube 32 is connected to the sample cell 24 and the other end (not shown) thereof can be connected to a pump (not shown) to feed a cleaning fluid to the sample cell 24 for purging the sample held therein through the open part 30 and can also be connected to a vacuum source (not shown) such as an aspirator for introducing a new sample from the sewage 14 into the sample cell 24 through the open part thereof. It is apparent that the thickness of the sample cell 24 is preferably as small as practical, whereby the sample can be statically held in the sample cell 24.

Since it is possible to freely bend the transparent window means 20, as shown by the phantom lines in FIG. 8, the sampling point can be freely selected in the sewage 14. It is apparent that the microorganism monitoring apparatus shown in FIGS. 8 to 10 operates in the same manner as in the embodiment shown in FIGS. 1 to 4. Of course, in this case, air, water or a part of the sewage 14 can likewise be used as the cleaning fluid.

Figure 11:
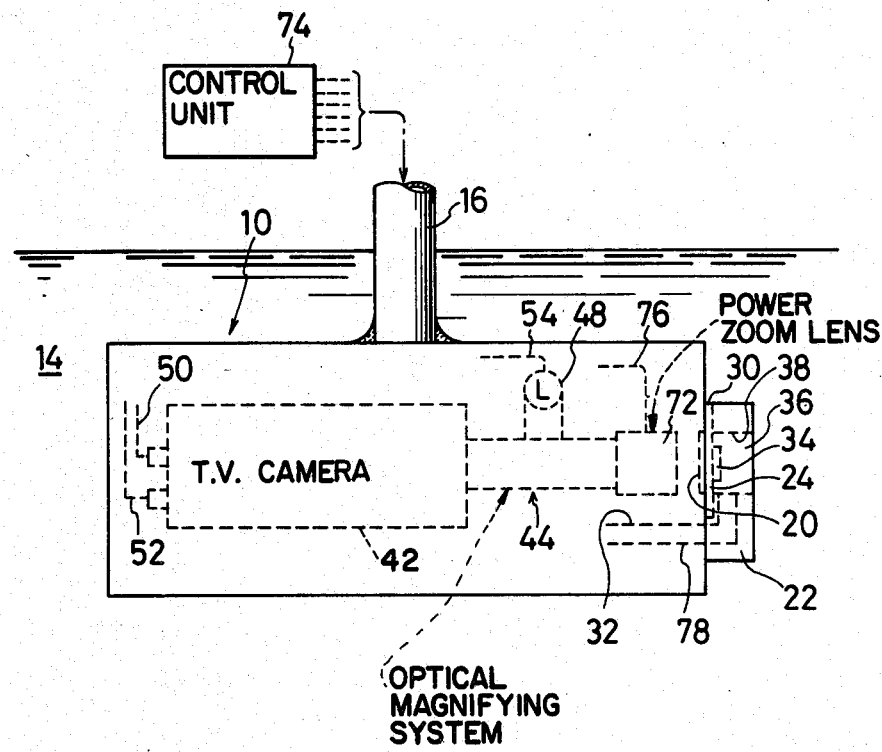
FIG. 11 is an elevational view showing a cylindrical closed housing which is similar to that of FIG. 1, in accordance with still another embodiment of the present invention.

FIG. 11 shows still another embodiment of the microorganism monitoring apparatus according to the present invention, wherein like reference numerals are used to designate the same elements as in the embodiments described above.

This microorganism monitoring apparatus is essentially the same as the embodiment shown in FIGS. 1 to 4 except that the magnifying power of the optical magnifying system 44 is adjustable and the disc-like insert 36 supporting the mirror 34 is movably mounted on the plate member 22 to permit adjustment of the space between the mirror 34 and the window glass 20.

In this embodiment, the optical magnifying system 44, which is combined with a TV camera as a part thereof, includes a power zoom lens 72 so that the magnifying power thereof can be changed. The power zoom lens 72 is connected to a control unit 74 through a wire 76. The control unit 74 may be placed at a monitoring station (not shown) and the wire 76 is led from the power zoom lens 72 to the control unit 74 through a hollow support rod 16. In this way, the power zoom lens 72 is controlled from the control unit 74 to adjust the magnifying power of the optical magnifying system 44. In addition, cables 50 and 52 for the TV camera 42 and a wire 54 for a light source 48 are also led to the control unit 74 through the hollow support rod 16 whereby the TV camera 42 and the light source 48 can be controlled from the control unit 74.

In order to movably mount the disc-like insert 36 supporting the mirror 34 in the plate member 22 for adjusting the space between the mirror 34 and the window glass 20, the disc-like insert 36 is threaded into a threaded bore 38 of the plate member 22 and is rotated by a servomotor (not shown) associated therewith. This servomotor is connected to the control unit 74 through a wire 78 which is led to the control unit 74 through the hollow support rod 16, whereby the servomotor can be controlled from the control unit 74.

In this embodiment, when the magnification of the image of the microorganisms is increased by the power zoom lens 72, the space between the mirror 34 and the window glass 20 is narrowed and the output of the light source 48 is simultaneously increased in response to the increase in the magnifying power so that the image of the microorganisms is always clearly and stably displayed on a display device such as a monitor TV. When the magnification of the image of the microorganisms is increased, it is necessary to narrow the space between the mirror 34 and the window glass 20 because the movement of the microorganisms is also magnified as the magnification increases. Also, when the magnification is increased, the depth of field of the optical magnifying system 44 is reduced so that images of the microorganisms, dregs, dirt or the like which are outside the depth of field appear as fuzzy images in the background of the focused image displayed on the monitor TV. However, this fuzzy background can be eliminated by narrowing the space between the mirror 34 and the window glass 20. Furthermore, as the magnification is increased, the image brightness is reduced, but this can be avoided by increasing the output of the light source 48. In this way, although the magnifying power of the optical magnifying system 44 is adjustable, it is possible to clearly and stably display the magnified image on the monitor TV. In addition, it is apparent that the monitoring operation is performed in the same manner as in the embodiment shown in FIGS. 1 to 4.

In the microorganism monitoring apparatus shown in FIG. 11, in general, the magnifying power of the magnifying system 44 may be adjusted within the range between 100 and 1000 times, but the present invention is of course not restricted to this range.

In the embodiment of FIG. 11, the plate member 22 per se may be moved in place of the movement of the insert 36. In addition, the adjustment of the space between the window glass 20 and the mirror 34 also serves to facilitate the cleaning of the surfaces of the window glass 20 and the mirror 34 because when the space is widened, the cleaning fluid can be sufficiently passed therethrough.

FIG. 12 shows a modified embodiment of the microorganism monitoring apparatus shown in FIG. 11, wherein like reference numerals are used to designated the same elements as in the embodiment of FIG. 11. In this modified embodiment, the TV camera 42 with the optical magnifying system 44 is movably supported by a power support device 80 from which a wire 82 is led to the control unit 74 through the hollow support rod 16 so that the power support device 80 can be controlled from the control unit 74. The TV camera 42 with the optical magnifying system 44 is moved by the power support device 80 in parallel with the window glass 20 so that the field of view obtained from the TV camera 42 can be changed. According to this embodiment, if the field of view under observation includes a zone which is desired to be observed more minutely at a higher magnification, the TV camera 42 can be moved so that the zone to be further magnified can be aligned with the optical axis thereof. That is, the zone can be moved to the center of the field of view.

FIG. 13 shows another modified embodiment of the microorganism monitoring apparatus shown in FIG. 11, wherein like reference numerals are used to designate the same elements as in the embodiment of FIG. 12. In this embodiment, the power support device 80 is mounted on the outside of the closed cylindrical housing 12. The power support device 80 serves to move the TV camera 42 with the optical magnifying system 44 not only within a plane parallel with the window glass 20, but also within a plane perpendicular to the window glass 20. According to this embodiment, when the optical magnifying system 44 comes to be focused at a point deviating from the correct point as a result of changing the magnifying power thereof, it is possible to shift the focus of the optical magnifying system 44 to the correct point by moving the TV camera 42 within the plane which is perpendicular to the window glass 20.

In the embodiments shown in FIGS. 12 and 13, it is apparent that the light source 48, the servomotor for moving the disc-like insert 36, and the power support device 80 can be automatically controlled in response to changes in the magnifying power of the optical magnifying system 44.

Figure 14:
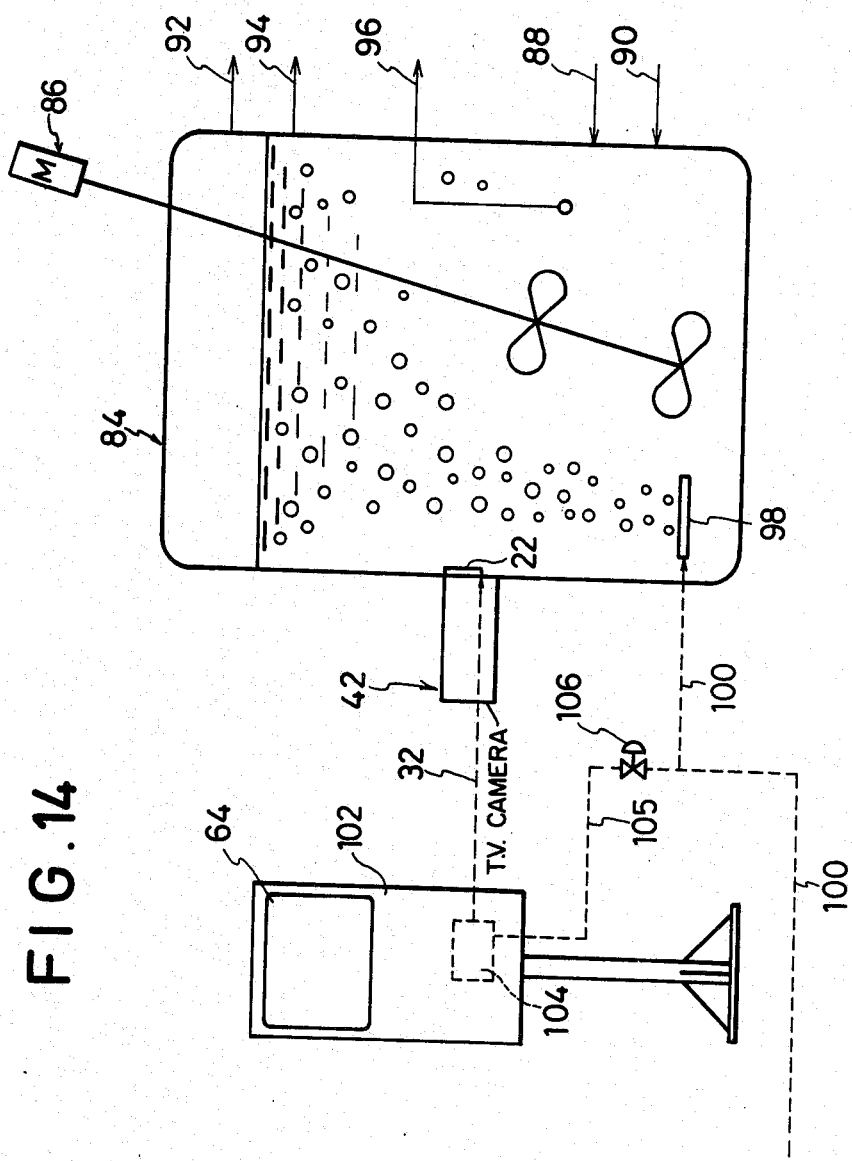
FIG. 14 is a diagrammatic view showing still another embodiment of the present invention, wherein the present invention is applied to a bioreactor.
Figure 15:
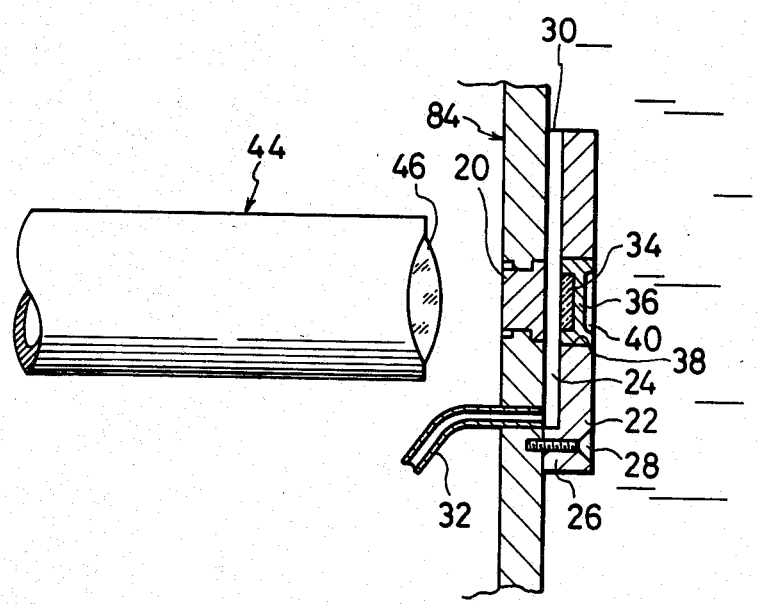
FIG. 15 is a partial sectional view showing the transparent window means used in the embodiment of FIG. 14.

FIGS. 14 and 15 shows still another embodiment of the microorganisms monitoring apparatus according to the present invention, wherein like reference numerals are used to designate the same elements as in the embodiments described above.

In FIGS. 14 and 15, the microorganism monitoring apparatus according to the present invention is applied to a bioreactor in which, for example, an antibiotic substance is produced by fermentation. In general, since the bioreactor has to be protected against invasion of sundry germs, it comprises a tightly sealed vessel or tank 84 as shown in FIG. 14. The sealed tank 84 receives a liquid to be treated and has an agitator 86 which is used to agitate the liquid and which includes a motor, an input shaft extending from the motor into the sealed tnak 84, and impellers attached to the free end of the shaft, as diagrammatically shown in FIG. 14. The sealed tank 84 includes two conduits 88 and 90 for feeding raw materials thereto to form the liquid to be treated, two conduits 92 and 94 for taking out a product gas and a product liquid from the tank 84, and a conduit 96 for taking out the liquid under treatment from the sealed tank 84, if necessary. The sealed tank 84 also has an air diffuser 98 disposed therein, since the antibiotic substance is commonly produced by aerobic bacteria. In order to feed sterilized air to the air diffuser 98, there is provided a conduit 100 one end of which is connected to the air diffuser 98 through the wall of the tank 84 and the other end of which is connected to a sterilized air source (not shown).

In the embodiment shown in FIGS. 14 and 15, transparent window means or window glass 20 is mounted in the wall of the closed tank 84 so that one face thereof is contacted with the liquid in the tank 84. A plate member 22 which is constructed in the same manner as in the embodiment shown in FIGS. 1 to 4 is mounted on the inner wall surface of the tank 84 by means of screws 28 so that the plate member is opposed to the one face of the window glass 20 to form a sample cell 24 therebetween. A disc-like insert 36 supporting a mirror 34 is threaded into a threaded bore 38 formed in the plate member 22 so that the surface of the mirror 34 is opposed to the one face of the window glass 20.

A TV camera 42 having an optical magnifying system 44 combined therewith is provided on the side of the other face of the window glass 20 so that an objective lens 46 of the optical magnifying system 44 is opposed to the other face of the window glass 20. The TV camera 42 is connected to a display device such as a monitor TV 64 through a cable (not shown in this embodiment). The monitor TV 64 is installed in a control panel 102 which is located at a monitoring station (not shown).

In order to purge a sample held in the sample cell 24 through an upper opening 30 thereof, there is provided a tube member 32 one end of which is connected to the sample cell 24 and the other end of which is connected to a pump 104 which is provided in the control panel 102. As shown in FIG. 14, the pump 104 is connected to the conduit 100 through a conduit 105 provided with a valve 106.

As will be apparent from the arrangement mentioned above, since sterilized air from the same source as that used in the bioreactor is utilized as a cleaning fluid for purging the sample from the sample cell 24, it is unnecessary to specially supply a separately sterilized cleaning fluid such as air or water. In other words, it is unnecessary to provide special equipment for sterilizing the cleaning fluid. If anaerobic bacteria are used in the bioreactor, that is, if the sterilized air source is not used, it is possible to utilize a raw material, the product gas, the product liquid or the liquid under treatment as the cleaning fluid so that the bioreactor is protected against invasion of sundry germs. In this case, of course, the conduit 105 extending from the pump 104 is instead connected to one of the conduits 88 to 96. Also, the other end of the tube member 34 can be selectively connected to a vacuum source such as an aspirator (not shown) for introducing a new sample into the sample cell 24 after the purging.

It is apparent that the monitoring operation by this embodiment is performed in the same manner as in the embodiment shown in FIGS. 1 to 4 except that the sampling point is fixed because the window glass 20 is mounted in the wall of the closed tank 84.

Figure 16:
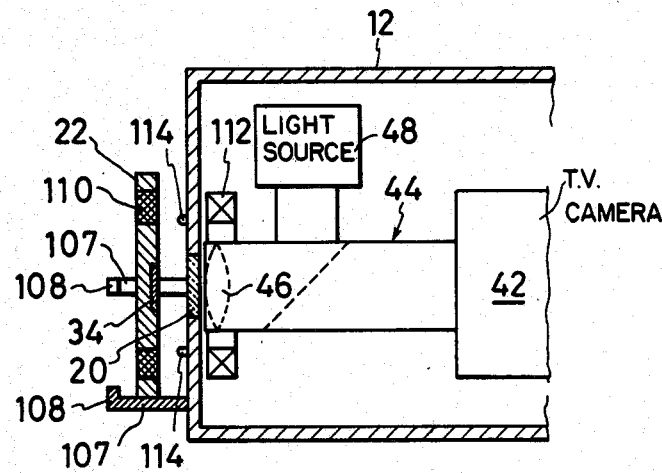
FIG. 16 is a partial longitudinal sectional view showing a box-like closed housing which is adapted to be submerged in a liquid contained in a vessel, in accordance with still another embodiment of the present invention.
Figure 17:
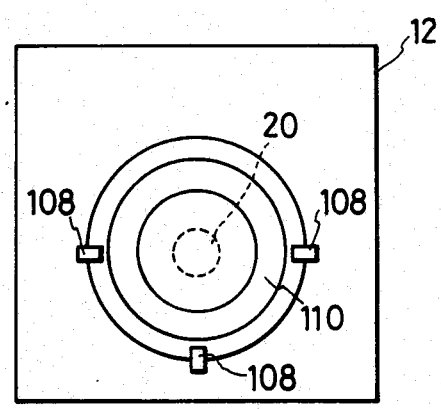
FIG. 17 is an end view of the box-like closed housing shown in FIG. 16.

FIGS. 16 and 17 show still another embodiment of the microorganisms monitoring apparatus according to the present invention, wherein like reference numerals are used to designate the same elements as in the embodiment shown in the FIGS. 1 to 4.

This apparatus is intended for use in a liquid which is treated by anaerobic bacteria or in a bioreactor such as shown in FIGS. 14 and 15 which has to be protected against invasion by sundry germs.

The apparatus comprises a box-like closed housing 12 which is adapted to be submerged in the liquid mentioned above. The housing 12 may be suspended in the same manner as in the embodiment shown in FIGS. 1 to 4 so that it can be freely moved within the liquid. A window glass 20 is mounted in the end face of the box-like housing 12 so that one face of the window glass 20 is contacted with the liquid. A TV camera 42, an optical magnifying system 44 combined with the TV camera 42, and a light source 48 combined with the optical magnifying system 44 are housed within the box-like housing 12 so that an objective lens 46 of the optical magnifying system 44 is opposed to the other face of the window glass 20.

A disc-shaped plate member 22 is disposed opposite to the one face of the window glass 20 and is movably supported by three guide members 107 which extend perpendicularly from the end face of the box-like housing 12 so as to contact the circumference of the disc-shaped plate member 22. Each guide member 107 has a projection 108 formed at its free end so that the plate member 22 is prevented from moving beyond the ends of the guide members 107 upon moving away from the end face of the housing 12. The plate member 22 has a mirror 34 which is opposed to the one face of the window glass 20, and also has an annular magnet 110 which is disposed around the mirror 34. An annular electromagnetic coil 112 is housed within the box-like housing 12 and is disposed opposite to the annular magnet 110 so that the plate member 12 can be vibrated by energizing the electromagnetic coil 112 in such a manner that a direct current is alternatively passed therethrough by using, for example, a switch. On the other hand, it is also possible to attract the plate member 22 toward the end face of the housing 12 by energizing the electromagnetic coil 112 with a direct current. At least three small projections 114 are provided on the end face of the housing 12 to surround the window glass 20 whereby a narrow space is formed between the plate member 22 and the end face of the housing 12 inclusive of the one face of the window glass 20 when the plate member 22 is attracted toward the end face of the housing 12.

In operation, when the plate member 22 is attracted toward the end face of the housing 12 to form the narrow space, a sample is statically held in the narrow space so that it can be observed and monitored in the same manner as in the embodiment shown in FIGS. 1 to 4. By vibrating the plate member 22, the sample can be purged from the narrow space while the surface of the mirror 34 and the one face of the window glass 20 are cleaned and are prevented from being smudged with dregs, dirt or the like included in the sample. When the plate member 22 is again attracted toward the end face of the housing 12, a new sample is held in the narrow space. Accordingly, since no cleaning fluid such as air is required for the purging and cleaning operations, this microorganism monitoring apparatus is suitable for use in a liquid which is to be treated with anaerobic bacteria or in a bioreactor which has to be protected against invasion of sundry germs.

In the embodiment shown in FIGS. 16 and 17, it is apparent that the small projections 114 may alternatively be provided on the face of the plate member 22 which is opposed to the end face of the housing 12.

Figure 18:
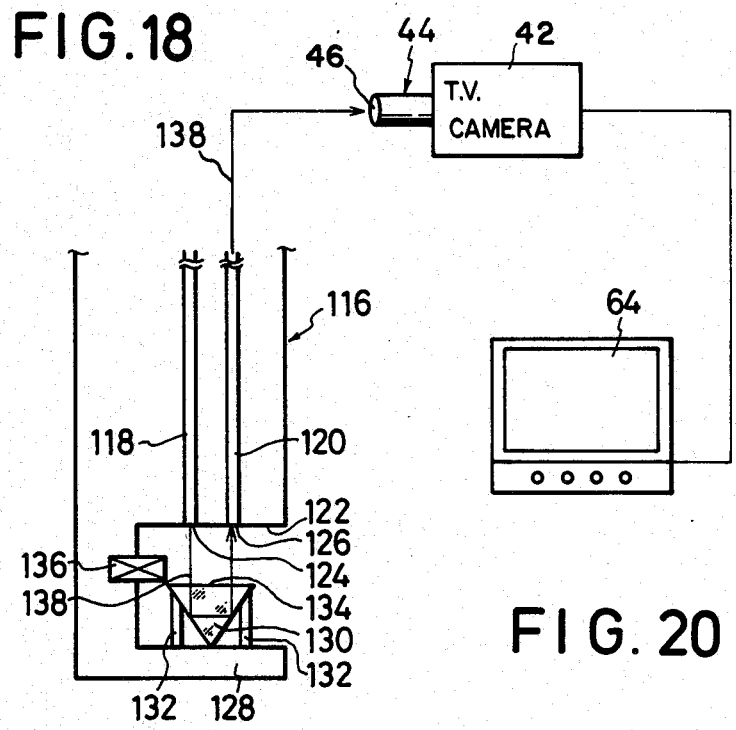
FIG. 18 is a diagrammatic view showing still another embodiment of the present invention in which a refraction means such as a triangular prism is used.

FIG. 18 shows still another embodiment of the microorganism monitoring apparatus according to the present invention, wherein like reference numerals are used to designate the same elements as in the embodiments described above.

This apparatus is also intended to be used in a liquid to be treated with anaerobic bacteria or in a bioreactor which has to be protected against invasion by sundry germs.

The apparatus comprises an elongate housing 116 including a light guide 118 and an optical image guide 120 therewithin. The elongate housing 116 has a free end face 122 adapted to be contacted with the liquid. The light guide 118 and the optical image guide 120 extend through the housing 116 so that their respective free end faces 124 and 126 are flush with the end face 122 of the housing 116. That is, the end faces 124 and 126 are exposed at the end face 122 of the housing 116. A light source (not shown in this embodiment) is provided at the other end face (not shown) of the light guide 118. A TV camera 42 which has an optical magnifying system 44 combined therewith is disposed at the other end face (not shown) of the optical image guide 120 so that an objective lens 46 of the optical magnifying system 44 is opposed to the other end thereof. The optical image guide 120 may be formed of a bundle of optical fibers or of an optical glass as used in the embodiment of FIGS. 5 to 7.

The apparatus also comprises a plate member 128 which is formed as an extended portion of the free end of the elongate housing 116. The plate member 128 is disposed opposite to the end face 122 of the housing 116 so as to form a sample cell between itself and the end face 122. As shown, a part of the sample cell is open to permit introduction of a sample of the liquid thereinto. A refractor 130 such as a triangular prism is supported by the plate member 128. More specifically, the triangular prism 130 is held between two support members 132 which extend from the plate member 128, and is disposed so that a flat face 134 thereof is opposed to the end face 122 of the housing 116 inclusive the end faces 124 and 126 so as to form a narrow space therebetween. It is apparent that although the sample introduced into the sample cell is statically held therein, a part of the sample present in the narrow space between the flat face 134 of the triangular prism 130 and the end face 122 of the housing 116 is more statically held. In order to replace the sample held in the sample cell with a new one, an ultrasonic vibrator 136 is provided in a part of the extended portion forming the plate member 128. The ultrasonic vibrator 136 also serves to prevent the flat face 134 of the prism 130 and the end face 122 of the housing 116 inclusive of the end faces 124 and 126 from being smudged with dregs, dirt or the like included in the sample.

It is apparent that this microorganism monitoring apparatus is also suitable for use in a liquid which is to be treated with anaerobic bacteria or in a bioreactor which has to be protected against invasion by sundry germs, for the same reasons as stated regarding the embodiment of FIGS. 16 and 17. In addition, it is apparent that the monitoring operation is performanced in the same manner as in the embodiment of the FIGS. 1 to 4 except that a light beam 138 emitted from the light source passes through the light guide 118 and is then introduced into the optical image guide 120 through the end face 126 thereof.

Figure 19:
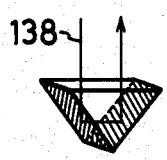
FIG. 19 is a perspective view showing a triangular prism with mirror faces, which can be used instead of the triangular prism used in the embodiment of FIG. 18.

FIG. 19 shows a triangular prism with mirror faces illustrated as hatched areas, which can be used in place of the prism 130 in the embodiment of FIG. 18. As shown, the light beam 138 is reflected by the mirror faces.

Figure 20:
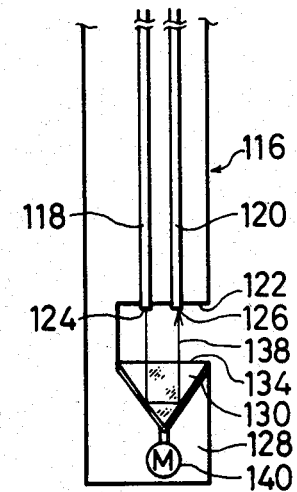
FIG. 20 is a diagrammatic view showing a modified embodiment of FIG. 18.

FIG. 20 shows a modified embodiment of the embodiment of FIG. 18, wherein like reference numerals are used to designate the same elements as in the embodiment shown in FIG. 18. In this modified embodiment, a cone-shaped prism 130 is used in place of the triangular prism and is rotatably seated in a cone-shaped recess formed in the plate member 128 so as to form a sample cell between a flat face 134 of the cone-shaped prism 130 and the free end face of the elongate housing 116 inclusive of the respective free end faces 124 and 126 of the light guide 118 and the optical image guide 120. The cone-shaped prism 130 can be rotated by a motor 140 embedded in the plate member 128. By rotating the cone-shaped prism 130, the sample held in the sample cell is replaced with a new sample and also the flat face 134 of the prism 130 and the end face 122 of the housing 116 inclusive of the end faces 124 and 126 are cleaned and are prevented from being smudged with dregs, dirt or the like included in the sample. It is apparent that this apparatus is essentially identical with the embodiment of FIG. 18 except that the purging of the sample and the cleaning of the sample cell are performed without using the ultrasonic vibrator.

In the embodiments shown in FIGS. 18 and 20, if desired the tube member described in connection with the embodiment shown in FIGS. 1 to 4 can be utilized for purging the sample from the sample cell and for introducing it thereinto. In this case, the tube member is housed within the elongate housing 116.

Also, to enable selection of the sampling point in the liquid, it is possible to form the elongate housing, the light guide and the optical image guide from flexible materials. When the tube member is used, it of course is also formed from a flexible material.

On the other hand, in the embodiments shown in FIGS. 1 to 17, it should be understood that the light source may be provided on the plate member. Also, in the embodiments shown in FIGS. 11 to 13, the window glass may be mounted in the wall of the vessel in which the liquid is received. Furthermore, in the embodiment shown in FIGS. 14 and 15, the window glass may be mounted in the wall of the closed housing as shown in the embodiment of FIGS. 1 to 4.

Finally, it should be understood that the microorganism monitoring apparatus according to the present invention can be utilized to observe and monitor minute inorganic particles present in a liquid without any modification thereof.

Although the present invention has been described in its preferred form with a certain degree of particularity, it is understood that the present disclosure of the preferred form can be changed in the details of construction and combination and arrangement of parts may be resorted to without departing from the spirit and the scope of the present invention as hereinafter claimed.

What we claim:

1. An apparatus for directly monitoring microorganisms present in a liquid, comprising:
   transparent window means, one face of which is adapted to be in contact with the liquid;
   a plate member disposed opposite to the one face of said transparent window means so as to form a narrow sample cell between said one face and a surface of said plate member, said sample cell being adapted to be submerged in the liquid to be monitored and having an opening to permit introduction and discharge of a sample from the liquid thereinto;
   a tube member, one end of which is connected to said sample cell and the other end of which can be connected to a source for a cleaning fluid to purge the sample held therein;
   a light source for directing a light beam onto the sample held in said sample cell;
   an optical magnifying system disposed opposite to the other face of said transparent window means to magnify an image of said microorganisms in the sample illuminated by said light beam; and
   means for observing the image magnified by said optical magnifying system.

2. An apparatus as set forth in claim 1, wherein said plate member has reflector means provided on its face opposed to the one face of said transparent window means, said light source is provided on the side of the other face of said transparent window means, the light beam emitted from said light source is guided through said optical magnifying system toward said reflector means, and said optical magnifying system receives the light beam reflected by said reflector means.

3. An apparatus as set forth in claim 1, wherein said light source is provided on the face of said plate member which is opposed to the one face of said transparent window means, and said optical magnifying system receives the light beam from said light source through said transparent window means.

4. An apparatus as set forth in claim 2, wherein said observing means includes a TV camera and a display device connected thereto, said transparent window means is mounted on a wall of a closed housing which is adapted to be submerged in the liquid, and said TV camera, said light source, said optical magnifying system and said tube member are housed within said closed housing.

5. An apparatus as set forth in claim 3, wherein said observing means includes a TV camera and a display device connected thereto, said transparent window means is mounted on a housing wall of a closed housing which is adapted to be submerged in the liquid, and said TV camera, said optical magnifying system and said tube member are housed within said closed housing.

6. An apparatus as set forth in claim 4, wherein said optical magnifying system is combined with said TV camera as a part thereof, the magnifying power of said optical magnifying system is adjustable, and said reflector means is movable to adjust the space between said reflector means and the one face of said transparent window means in response to the adjustment of the magnifying power.

7. An apparatus as set forth in claim 6, wherein said TV camera with the optical magnifying system is movable within a plane parallel with said transparent window means.

8. An apparatus as set forth in claim 7, wherein said TV camera is further movable within a plane perpendicular to said transparent window means.

9. An apparatus as set forth in claim 1, wherein the liquid is contained in a vessel, said transparent window means is mounted on the wall of said vessel.

10. An apparatus as set forth in claim 9, wherein said transparent window means comprises a cylindrical optical glass which extends through the wall of said vessel and which guides an image from its one end face to its other end face.

11. An apparatus as set forth in claim 1, wherein said transparent window means comprises a flexible bundle of optical fibers the free end face of which is immersed into the liquid through the surface thereof.

12. An apparatus as set forth in claim 1, wherein the liquid is in a vessel for a bioreactor, said transparent window means is mounted on the wall of said bioreactor vessel, and a raw material to be fed into said bioreactor vessel, a product obtained from said bioreactor vessel and/or a liquid contained in said bioreactor vessel is used as the cleaning fluid for purging the sample held in said sample cell.

13. An apparatus set forth in claim 1, wherein said plate member is movable to adjust a space between said plate member and the one face of said transparent window.

14. An apparatus as set forth in claim 2, wherein said reflector means is movable to adjust a space between said plate member and the one face of said transparent window.

15. An apparatus for directly monitoring microorganisms present in a liquid, comprising:
   transparent window means, one face of which is adapted to be in contact with the liquid;
   a plate member with a magnet disposed opposite to the one face of said transparent window means and being movable perpendicularly to said one face;
   spacer means provided between said plate member and the one face of said transparent window means so as to form a narrow intervening space for introducing a sample from the liquid thereinto;
   an electromagnetic coil provided on the side of the other face of said transparent window means to move said plate member perpendicularly to the one face of said transparent window means for purging the sample held in said narrow space and for introducing a new sample thereinto;
   a light source for directing a light beam onto the sample held in said narrow space;
   an optical magnifying system disposed opposite to the other face of said transparent window means to magnifying an image of the sample illuminated by said light beam; and
   means for observing the image magnified by said optical magnifying system.

16. An apparatus as set forth in claim 15, wherein said spacer means comprises at least three projections formed on the circumference of said transparent window means.

17. An apparatus as set forth in claim 15, wherein said spacer means comprises at least three projections formed on said plate member.

18. An apparatus as set forth in claim 15 wherein said plate member has reflector means provided on its face opposed to the one face of said transparent window means, said light source is disposed on the side of said transparent window means, the light beam emitted from said light source is guided through said optical magnifying system toward said reflector means, and said optical magnifying system receives the light beam reflected by said reflector means.

19. An apparatus as set forth in claim 15 wherein said light source is provided on the face of said plate member which is opposed to the one face of said transparent window means, and said optical magnifying system receives the light beam from said light source through said transparent window means.

20. An apparatus as set forth in claim 18, wherein said observing means includes a TV camera and a display device connected thereto, said transparent window means is mounted on a wall of a closed housing which is adapted to be submerged in the liquid, and said TV camera, said light source and said optical magnifying system are housed within said closed housing.

21. An apparatus as set forth in claim 19, wherein said observing means includes a TV camera and a display device connected thereto, said transparent window means is mounted on a wall of a closed housing which is adapted to be submerged in the liquid, and said TV camera and said optical magnifying system are housed within said closed housing.

22. An apparatus as set forth in claim 15, wherein the liquid is contained in a vessel, said transparent window means is mounted on the wall of said vessel.

23. An apparatus as set forth in claim 18, wherein said transparent window means is mounted on the wall of said vessel.

24. An apparatus as set forth in claim 19, wherein said transparent window means is mounted on the wall of said vessel.

25. An apparatus as set forth in claim 15, wherein said transparent window means comprises a flexible optical image guide the free end face of which is immersed into the liquid through the surface thereof.

26. An apparatus as set forth in claim 18, wherein said transparent window means comprises a flexible bundle of optical fibers the free end face of which is immersed into the liquid through the surface thereof.

27. An apparatus as set forth in claim 19, wherein said transparent window means comprises a flexible bundle of optical fibers, a free end face of said bundle being immersed into the liquid through the surface thereof.

28. An apparatus for directly monitoring microorganisms present in a liquid, comprising:
   an elongate housing including a light guide and an optical image guide therewithin and having a free end face adapted to be in contact with the liquid, said light guide and said optical image guide extending to the free end face of said elongate housing so that respective free end faces of said light guide and said optical image guide are exposed at the free end face of said elongate housing;
   a plate member formed as an extended portion of the free end of said elongate housing and disposed opposite to the free end face of said elongate housing so as to form a sample cell there between, a part of said sample cell being open to permit introduction of a sample from the liquid thereinto;

a refractor means supported by said plate member and having a flat face which is opposed to the free end face of said optical image guide so as to form a narrow space therebetween;

a light source provided on the other end face of said light guide;

said refractor means being arranged in such a manner that after a light beam emitted from said light source passes through said light guide, it is introduced into said optical image guide through the exposed end face thereof;

an optical magnifying system provided on the other end face of said optical image guide to magnifying an image of the sample illuminated has the light beam introduced into said optical image guide;

means for observing the image magnified by said optical magnifying system; and means for purging the sample held in said sample cell and for introducing a new sample thereinto.

29. An apparatus as set forth in claim 28, wherein said purging and introducing means comprises a ultrasonic vibrator provided in said sample cell.

30. An apparatus as set forth in claim 28, wherein said purging and introducing means comprises a motor for rotating said refractor means.

31. An apparatus as set forth in claim 26, wherein said purging and introducing means comprises a tube member one end of which is connected to said sample cell and the other end of which can be connected to a source for a cleaning fluid to purge the sample held therein.

32. An apparatus as set forth in claim 31, wherein said tube member is housed in said elongate housing.

33. An apparatus as set forth in claim 28, wherein said elongate housing, said light guide and said optical image guide are flexible.

34. An apparatus as set forth in claim 31, wherein said elongate housing, said light guide, said optical image guide and said tube member are flexible.

* * * * *